United States Patent
Huang et al.

(10) Patent No.: US 9,056,091 B1
(45) Date of Patent: Jun. 16, 2015

(54) COMPOSITION FOR REGULATION OF LIVER X RECEPTOR

(71) Applicant: National Taiwan University, Taipei (TW)

(72) Inventors: Ching-jang Huang, Taipei (TW); Meng-ting Wu, Taipei (TW); Hong-nong Chou, Taipei (TW); Mei-ling Chang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/305,209

(22) Filed: Jun. 16, 2014

(30) Foreign Application Priority Data

Mar. 3, 2014 (TW) .............................. 103107078 A

(51) Int. Cl.
  *C07D 303/00* (2006.01)
  *A61K 31/336* (2006.01)
  *A61K 31/18* (2006.01)
  *A61K 31/195* (2006.01)

(52) U.S. Cl.
  CPC ............... *A61K 31/336* (2013.01); *A61K 31/18* (2013.01); *A61K 31/195* (2013.01)

(58) Field of Classification Search
  CPC .. C07D 303/14; C07D 303/16; C07D 303/17; A61K 31/336; A61K 31/18; A61K 31/195
  USPC ................................................... 549/546, 547
  See application file for complete search history.

(56) References Cited

PUBLICATIONS

Tsukui et al, Fucoxanthin and Fucoxanthinol enhance the Amount of Docosahexaenoic Acid in the Liver of KKAy Obese/Diabetic Mice, 2007, J. Agric. Food Chem. , 55, p. 5025-5029.*
Beppu et al , Effects of dietary fucoxanthin on cholesterol metablosim in diabetic/obses KK-Ay mice, Lipids in Health and Disease, 2012, 11:112, p. 1-8.*
Jui-Che Chen, "Isolation and structure elucidation of natural products from Hincksia mitchellae(harvey) P.C. silva", Master thesis of Department of Fisheries Science, National Taiwan University, Jan. 2007 [Relevant pages : p. 15(figure 3) and p. 69(table 2)].

* cited by examiner

*Primary Examiner* — T. Victor Oh
(74) *Attorney, Agent, or Firm* — WPAT, P.C.; Anthony King

(57) ABSTRACT

The present invention provides a composition for the regulation of Liver X Receptor (LXR) in a cell, and the composition comprises fucoxanthin and its metabolite, fucoxanthinol. The composition of the present invention regulates the transactivation activity of LXR in cell, and antagonizes the transactivation activity of LXRα and/or LXRβ induced by LXR agonists. In other aspects, the present invention also provides a method of regulating a liver X receptor. The composition for the regulation of liver X receptor and the application thereof according to the present invention can regulate the transactivation activity of LXR in cell, and can further be used as alternatives for LXR agonist or antagonist, or supplements, for enhancing LXR-related symptoms.

5 Claims, 2 Drawing Sheets

COMPOSITION FOR REGULATION OF LIVER X RECEPTOR

CROSS-REFERENCES TO RELATED APPLICATIONS

This application claims priority to Taiwan Patent Application No. 103107078 filed on 3 Mar. 2014. All disclosure of which is incorporated herein by reference in its entirety.

BACKGROUND OF THE INVENTION

1. Field of the Invention

The present invention is related to a composition for regulation of liver X receptor and applications thereof, and the composition comprises fucoxanthin and a metabolite thereof, fucoxanthinol.

2. The Prior Arts

There are various types of photosynthetic pigments in algae, such as chlorophyll, carotene, phycocyanin, phycoerythrin, xanthophyll, etc. *Laminaria japonica* (seaweed) and *Undaria pinnatifida*, in particular, are rich in fucoxanthin. Fucoxanthin is an orange-yellow color pigment and unique type of carotenoid found in marine creatures. Previous studies had indicated that, in white adipocytes, fucoxanthin can enhance the activation of Uncoupling protein 1 (UCP1) which breaks down fat tissues and generates brown adipocytes with energy consuming ability. Fucoxanthin can also promote liver to produce docosahexanenoic acid (DHA) and lower the low-density lipoprotein associated with obesity and cardiovascular diseases. Moreover, fucoxanthin is also proven to be able to regulate many kinds of energy-promoting genes in mitochondria.

Liver X receptor (LXR) is a member of the nuclear receptor family and includes two subtypes with similar structure, namely LXRα and LXRβ. The amino acid sequences of the DNA binding domain and ligand binding domain of these two subtypes exhibit 77% consistency. LXRα can be found only in few organ and tissues such as liver, small intestine, adipocytes, and macrophage, whereas LXRβ are distributed throughout almost the entire body. The mechanism of LXR is similar to those of classic nuclear receptors. Upon the ligand binds to and activates LXR, LXR undergoes structural transformation and forms heterodimer with retinolid X receptor (RXR). The LXR-RXR heterodimer then enters the nucleus and binds with DNA, which is the LXR response element (LXRE) of the promoter of the target gene, thus, drives transcription. According to researches, LXRα agonist can reduce the precipitation of cholesterol in blood vessels via activation of LXR. Experimentations had indicated that, if the LXRα gene of mice was knocked out, the mice can remain normal when fed with normal diet; however, when the mice were fed with diet with exceeded cholesterol, fatty liver disease and blood vessel blockage occurred. On the other hand, there were also studies shown that agonist of LXR can inhibit growth of carcinoma cells. Artificial LXR agonist T0901317 (N-(2,2,2-trifluoroethyl)-N-[4-[2,2,2-trifluoro-1-hydroxy-1-(trifluoromethyl)ethyl]phenyl]-benzenesulfonamide) can bind most strongly to LXR; thus, can inhibit the growth of carcinoma cells to the greatest extend. As a result, carcinoma cells with higher LXR expression are more likely to be inhibited by LXR agonist. When LXR were introduced to carcinoma cells with low LXR expression for overexpression, cells not likely to be inhibited by LXR agonist changed into those likely to be inhibited by LXR agonist, indicating that the inhibitory effect is through LXR. Yet, artificial LXR agonist, the abovementioned T0901317 for example, causes side effects such as accumulation of triglyceride in liver when overdose.

The raw materials used in the present invention are fucoxanthin and its metabolite, fucoxanthinol, from those algae can be used for regulating LXR, which can serve as safe and side effect-free compositions of healthy food or pharmaceuticals for improving the symptoms caused by lacking LXR in cells.

SUMMARY OF THE INVENTION

As a result, the present invention provides a composition for the regulation of liver X receptor (LXR) comprising fucoxanthin and a metabolite thereof, wherein the metabolite of fucoxanthin is fucoxanthinol. In one embodiment of the present invention, the composition regulates the transactivation activity of the liver X receptor in a cell, wherein the liver X receptor is LXRα or LXRβ, and the composition enhances the transactivation activity of LXRβ. In another embodiment of the present invention, when the composition is co-administered with a LXR agonist to a subject, the composition antagonizes the transactivation activity of LXRα and/or LXRβ induced by the LXR agonist. The LXR agonist is N-(2,2,2-trifluoroethyl)-N-[4-[2,2,2-trifluoro-1-hydroxy-1-(trifluoromethyl)ethyl]phenyl]-benzenesulfonamide (T0901317) or 3-[3-[[[2-Chloro-3-(trifluoromethyl)-phenyl]methyl]-(2,2-diphenyl-ethyl)amino]propoxy]benzeneacetic acid (GW3965). The composition of the present invention is a pharmaceutical composition or a food composition.

Another aspect of the present invention is to provide a method of regulating a live X receptor (LXR), comprising administering to a subject an effective amount of fucoxanthin or a metabolite thereof, and the fucoxanthin or the metabolite thereof regulates the transactivatinon activity of the liver X receptor. The metabolite of fucoxanthin is fucoxanthinol. The liver X receptor is LXRα or LXRβ. In one embodiment of the present invention, the fucoxanthin or the metabolite enhance the transactivation activity of LXRβ. In another embodiment of the present invention, when the fucoxanthin or the metabolite is co-administered with a LXR agonist to the subject, the fucoxanthin or the metabolite antagonizes the transactivation activity of LXRα and/or LXRβ induced by the LXR agonist. The LXR agonist is N-(2,2,2-trifluoroethyl)-N-[4-[2,2,2-trifluoro-1-hydroxy-1-(trifluoromethyl)ethyl]phenyl]-benzenesulfonamide (T0901317) or 3-[3-[[[2-Chloro-3-(trifluoromethyl)phenyl]methyl](2,2-diphenyl-ethyl)amino]propoxy]benzeneacetic acid (GW3965).

The composition for regulation of liver X receptor of the present invention can effectively regulate the transactivation activity of LXR and, more specifically, the transactivation activity of LXRβ. Meanwhile, the composition for regulation of liver X receptor of the present invention can antagonize the transactivation activities of LXRα and/or LXRβ induced by LXR agonists. Furthermore, the composition for regulation of liver X receptor of the present invention can be used as an alternative or supplement for LXR agonist or antagonist for improving the symptoms associated with LXR activity.

The present invention is further explained in the following embodiment illustration and examples. Those examples below should not, however, be considered to limit the scope of the invention, and it is contemplated that modifications will readily occur to those skilled in the art, which modifications will be within the spirit of the invention and scope of the appended claims.

DETAILED DESCRIPTION OF THE PREFERRED EMBODIMENT

Definition

Figure 1:
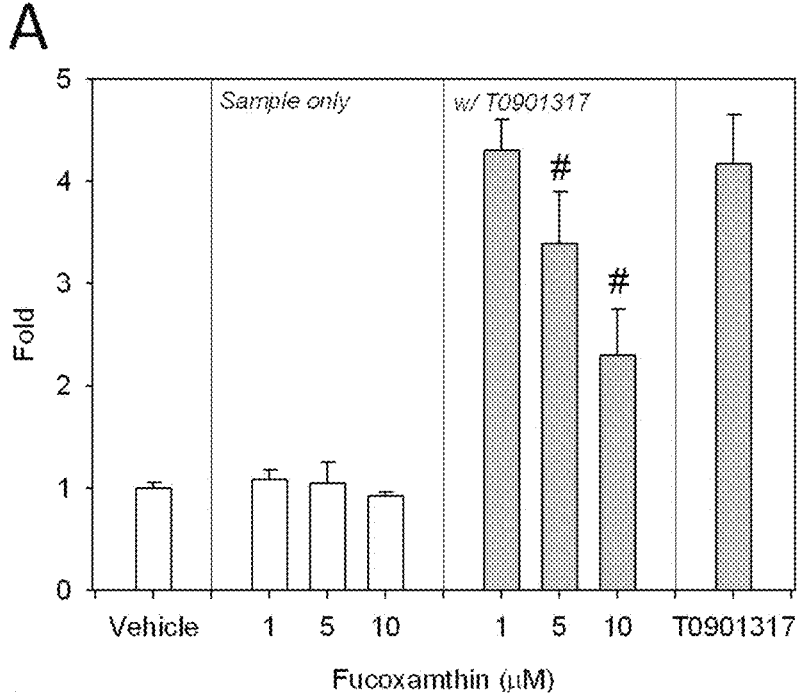
FIG. 1, the transactivation activities of fucoxanthin and fucoxanthinol for LXRα, wherein (A) represents the transactivation activity of fucoxanthin for LXRα; (B) represents the transactivation activity of fucoxanthinol for LXRα; # represents p<0.05, which indicates significant difference when comparing with the positive control.
Figure 1:
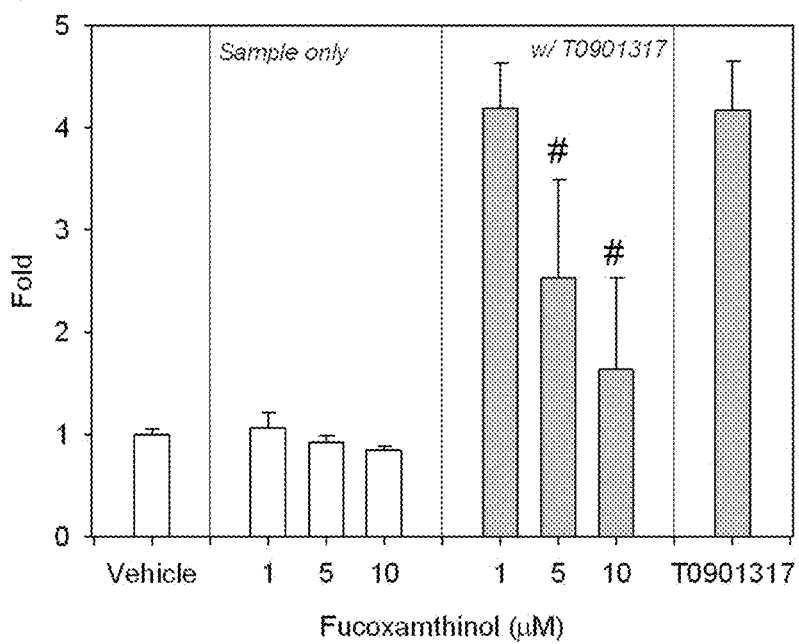

As used herein, the term "regulation" refers to the ability to increase or reduce activity. Hence, according to the method of regulating LXR of the present invention, the LXR is made to contact with the composition of the present invention. As further described in the embodiments, the composition of the present invention can be used to increase or reduce the transactivation activities of LXR in a subject which regulation of LXR is needed by administrating an effective amount of the composition of the present invention.

The term "agonist" refers to certain substances that can interact with and activate receptors, such as LXR, as well as trigger physiological or pharmaceutical responses and characteristics thereof.

As used herein, the terms "antagonist" and "antagonistic effect" mean certain substances that competitively bind to the receptor at the same position as the agonist but do not activate the responses of receptor activity; in fact, inhibit the physiological or pharmaceutical responses triggered by the agonist.

As used herein, the term "metabolite" refers to the metabolic products of fucoxanthin or the pharmaceutical acceptable salts, similar compound or derivatives thereof which have effects similar to those of fucoxanthin in living organism.

The embodiment of the present invention is to establish a method for effectively determining whether the sample has LXR transactivation activity, which comprise transfecting a cell which can select expression vectors having LXR transactivation activity, adding LXR agonist T0901317 and GW3965 (3-[3-[[[2-Chloro-3-(trifluoromethyl)phenyl]methyl](2,2-diphenyl-ethyl)amino]-propoxy]benzeneacetic acid) as positive controls and samples to be tested respectively to the culture medium during cell culture, and detecting the expression of the reporter genes on the expression vectors when the sample to be tested exhibits LXR transactivation activity. In the present invention, the samples to be tested are fucoxanthin and its metabolite, fucoxanthinol, isolated and purified from algae. The ability to regulate the transactivation activities of LXR of fucoxanthin and fucoxanthinol are further confirmed by the following embodiments. The above-mentioned method is explained in detail as follow:

Materials and Method
Incubation of Algae

The algae used in the present invention includes but not limit to *Padina minor, Dictyota divaricata, Sargassum cristaefolium, Laminaria japonica*, and *Hincksia mitchellae*, and preferably, *Hincksia mitchellae. Hincksia mitchellae* were harvested from the North-east coast of Taiwan. *Hincksia mitchellae* were incubated in SWM-III media and the composition of SWM-III media is shown in Table 1.

TABLE 1

| Ingredient | Amount required | Final concentration |
|---|---|---|
| $NaNO_3$ | 169.98 g | 2 mM |
| $K_2HPO_4$ | 24.07 g | 0.1 mM |
| $Na_2 \cdot EDTA$ | 11.17 g | 30.1 μM |
| $FeCl_3 \cdot 6H_2O$ | 0.54 g | 2 μM |
| $H_3BO_3$ | 12.37 g | 200 mM |
| $MnCl_2 \cdot 4H_2O$ | 2.18 g | 10 mM |
| $ZnCl_2$ | 0.11 g | 0.8 mM |
| $CoCl_2 \cdot 6H_2O$ (20 mM)[1] | 1 mL primary stock | 20 μM |
| $CuCl_2 \cdot 2H_2O$ (0.2 mM)[2] | 1 mL primary stock | 0.2 μM |

[1] $CoCl_2 \cdot 6H_2O$ (20 mM) primary stock: 47.59 mg dissolved in 10 mL deionized water and preserved in 4° C.
[2] $CuCl_2 \cdot H_2O$ (0.2 mM) primary stock: 34 mg dissolved in 1 L deionized water and preserved in 4° C.

In the present invention, *Hincksia mitchellae* were incubated in 400 L aquarium with the addition of SWM-III media (1000×) to sea water. The algae were amplified and sub-cultured at the ratio of 1:4 to 1:2 during 2 to 3 weeks of incubation with pumped-air and light (Light:Dark=14:10). After incubation, wet algae was collected and washed to remove salt on the surface using clear water, then freeze-dried and grinded. On average, one aquarium yielded approximately 50 g of *Hincksia mitchellae* powder.

Extraction and Purification of Fucoxanthin 100 g of *Hincksia mitchellae* powder were collected and were stirred using acetone of 30 times volume in room temperature, extracted overnight and then underwent suction filtration to collect filtrate. After suction filtration, the remaining powder was extracted using acetone again. The filtrate of the two rounds suction filtration were combined and further concentrated under reduced pressure to give 9.85 g of acetone extract. Silica (silica gel 60, 230-400 mesh, Merck) of approximately 10 times the volume of the acetone extract was used to prepare silica column (internal diameter: 3 cm; height of silica: 25 cm), and the column was balanced using 45% ethyl acetate(EA)/hexane. The acetone extract was dissolved in small amount of EA and mixed with thick silica (Silica gel 60, 70-230 mesh, Merck). After dried by rotary evaporator, the thick silica covered with extract was placed on top of the balanced silica gel as describe above and were eluted using 45% EA/hexane. Red-colored fraction in the middle, namely Fucoxanthin-rich fracton-1, was collected. Fucoxanthin-rich fraction-1 weighted about 0.98 g after removing the solvent. Another silica gel column was used to separate fucoxanthin-rich fraction-1 again by the elusion of 19% acetone/1% ethanol/hexane. Orange-red-colored fraction in the middle, namely Fucoxanthin-rich fraction-2, was collect. Fucoxanthin-rich fraction-2 weighted about 0.44 g after removing the solvent. Fucoxanthin-rich fraction-2 was dissolved back in 45% acetone/hexane and was left to stand for 4 hours in −20° C. after the addition of distilled water of equivalent amount. Orange-red fucoxanthin powder of approximately 0.3 g was obtained by suction filtration, washing of distilled water to remove organic solvent, and freeze-drying. That is to say, every gram of dried algae can yield approximately 3 mg of fucoxanthin.

The above mentioned fucoxanthin obtained was identified using H-NMR and its purity was analyzed via HPLC-UV/VIS. The H-NMR analysis was performed at Instrumentation Center of National Taiwan Normal University and the above-mentioned purified product was confirmed to be fucoxanthin by comparison with the hydrogen spectral series of Chen 2007 (Master thesis of Department of Fisheries Science, National Taiwan University: Isolation and structure elucidation of natural products from *Hincksia mitchellae*(harvey) P.C. silva). For further HPLC analysis, UV/VIS detector (PU-980 pump, UV-visible absorbance detector, Jasco) and Reverse phase chromatography (LiChrospher® 100 RP-18 column, 5 μm, Merck) were used with eluting solution of methanol/$H_2O$ (90:10 v/v) at the flow speed of 1 mL/min. The absorbance of 450 nm was observed. After calculating with the standard curve plotted using standard product, the purity of the abovementioned purified fucoxanthin extract was more than 95%. The chemical structure of fucoxentin is illustrated as Formula I as follow:

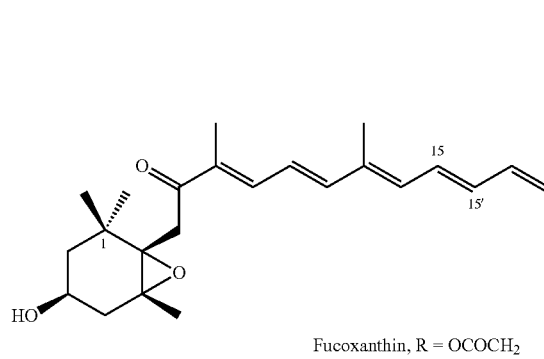
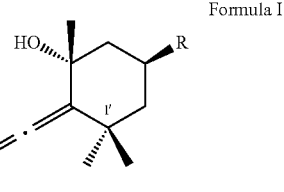

Formula I

Fucoxanthin, R = $OCOCH_2$

Preparation of Fucoxanthinol 2 mg of fucoxanthin and 10 mg of Taurocholic acid sodium salt were dissolved in a small amount of methanol and dried using nitrogen. Then, 8 mL of potassium phosphate buffer solution having 20 mg of lipase (from procine pancreas, Type II, Sigma L3126) were added. After reacting for 2 hours in 37° C., 1 mL of methanol and 2 mL of diethyl ether were added and the diethyl ether layer was purified using HPLC to give fucoxanthinol. The yield of fucoxanthinol was up to 20%. The chemical structure of fucoxanthinol is illustrated as Formula as follow:

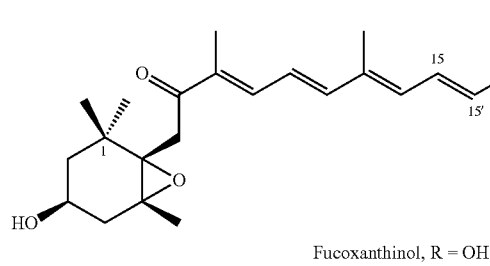
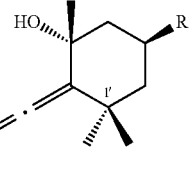

Formula II

Fucoxanthinol, R = OH

Detection of LXR Transactivation Activity

For the evaluation of LXR transactivation activity, the embodiments of the present invention utilize transient transfection and the vectors used are: (1) pBKCMV GAL4-hLXRα and pBKCMV GAL4-hLXRβ; (2) pBKCMV $(UAS)_4$-alkaline phosphatase, wherein pBKCMV GAL4-hLXRα and pBKCMV GAL4-hLXRβ are pBKCMV vectors having chimeric receptor of GAL4-hLXRα ligand binding doman (LBD) and GAL4-hLXRβ LBD, while pBKCMV $(UAS)_4$-alkaline phosphatase is the pBKCMV vector having the reporter gene of $(UAS)_4$ alkaline phosphatase (ALP). UAS indicates upstream activation sequence. All vectors were co-transfected into Chinese hamster ovary cell (CHO-K1, from Bioresource Collection and Research Center of Food Industry Research and Development Institute, BCRC: 6006). When the sample tested exhibits LXR transactivation activity, it reacts with LXR and triggers the specific binding of GAL4 to the UAS on the receptor gene, thus promotes the expression of alkaline phosphatase reporter gene. Hence, LXR transactivation activity of the sample can be determined by detecting the expression of ALP.

Example 1

Cell Culture and Transient Transfection

1. Cell Culture

CHO-K1 is attached cell. Firstly, CHO-K1 cells were incubated using Ham's F-12 medium (HAM, GIBCO, 11765) having 10% FBS (GIBCO, 10437), 10% FBS-Ham's F12. Sub-culturing was performed every 3 to 4 days when cell growth reached about 90% confluency. Method for sub-culturing is describe as follow: Removing culture medium; washing the cell twice using 1× PBS; suspending the cells using 0.2 mL trypsin-EDTA solution (0.25% Trypsin, 1 nM EDTA.4Na, 1× liguid, GBICO, 25200) in each 25 $cm^2$ flask. Flasks were then slightly shaken to moisture all cells then were placed in incubation chamber for 3 minutes at 37° C. with 5% $CO_2$. 3 mL of 10% FBS-Ham's F-12 medium were collected and cells were washed off. $3 \times 10^5$ cells were seeded into 25 $cm^2$ flask preloaded with 5 mL of 10% FBS-Ham's F-12 medium and were incubated at 37° C. with 5% $CO_2$. Sub-culturing was repeated after 3 to 4 days as described above.

2. Transient Transfection

Transient transfection of the embodiments of the present invention was performed using Lipofectamin 2000 (Invitrogen). Firstly, after CHO-K1 cells were fully grown, cells were dis-attached by trpsin-EDTA solution and were eluted using 10% CSF-Ham's F-12, wherein CSF represents the FBS pretreated by charcoal (Dextran coated, Sigma, C6231). The cell suspension was diluted to $2.5 \times 10^5$ cells/mL, planted onto 96-well plate (100 μL/well), and incubated for 20 to 24 hours at 37° C. with 5% $CO_2$. The conditions for transfection are shown in Table 2.

TABLE 2

| Conditions | LXRα | LXRβ |
|---|---|---|
| Lipofectamine 2000 (μL/well) | 0.8 | 0.8 |
| pBKCMV vector having receptor (μg/well) | 0.2 | 0.2 |
| pBKCMV vector having reporter gene (μg/well) | 0.05 | 0.05 |
| Standards | T0901317 | GW3965 |
| Treating concentration | 0.5 μM | 0.5 μM |

Detailed steps for transfection are as follow: Lipofectamine 2000 was diluted in PS tubes by serum-free OPTI-MEM®I (GIBCO, 31985) for 5 minutes at room temperature; the vector DNA was diluted by a small amount of serum-free OPTI-MEM®I; the vectors in Table 2 were mixed with Lipofectamine 2000 with specific ratio (GAL4-hLXRα:(UAS)$_4$-ALP=4:1; GAL4-hLXRβ:(UAS)$_4$-ALP=4:1) and reacted for 20 minutes at room temperature. During the reaction, the cells were washed by serum-free Ham's F-12 medium (100 μL/well) twice to allow the formation of DNA-liposome complex; the vectors were then added to the above washed cells for transfection to take place at 37° C. and 5% $CO_2$. Solution for transfection was removed after the transient transfection was completed.

Example 2

Fucoxanthin and Fucoxanthinol Regulate the Transactivation Activity of LXRα

Cells after transient transfection in Example 1 and removing the transfection solution were added to fucoxanthin and fucoxanthinol diluted with 10% TCM-Ham's F-12, LXR agonist T0901317, or none, to serve as experimental group, positive control, or vehicle, respectively. The ALP activities of all groups were analysis after incubation for 48 hours at 37° C. with 5% $CO_2$.

The ALP activity analysis was performed by reacting the culture medium (20 μL/well) and reactant (100 mM pNPP: $H_2O$:2X SEAP assay buffer=1:9:10, 200 μL/well) in a new 96-well plate for 15 minutes at 37° C. The absorbance at 405 nm was measured using microspectrometer.

The analytical results of transactivation activities of fucoxanthin and fucoxanthinol for LXRα are shown in FIG. 1. As shown in FIG. 1(A), no significant LXRα transactivation activities ($p>0.05$) were observed for fucoxanthin at 1, 5, and 10 μM; when co-treated with LXR agonist T0901317, the positive control, 5 and 10 μM of fucoxanthin significantly reduced the LXRα transactivation activity to 76% and 41% of T0901317, respectively ($p<0.05$). On the other hand, as shown in FIG. 1(B), no significant LXRα transactivation activities ($p>0.05$) were observed for fucoxanthinol at 1, 5, and 10 μM either; likewise, when co-treated with LXR agonist T0901317, the positive control, 5 and 10 μM of fucoxanthinol also significantly reduced the LXRα transactivation activity to 48% and 20% of T0901317, respectively ($p<0.05$).

According to this embodiment, for LXRα, neither fucoxanthin nor fucoxanthinol shows significant effect on enhancing the transactivation activity of LXRα; however, both fucoxanthin and fucoxanthinol show significant antagonistic effects against LXR agonist T0901317. Among which, fucoxanthin in particular shows more preferable antagonistic effect.

Example 3

Fucoxanthin and Fucoxanthinol Regulate the Transactivation Activity of LXRβ

Cells after the abovementioned transient transfection and removing the transfection solution were added to fucoxanthin and fucoxanthinol diluted with 10% TCM-Ham's F-12, LXR agonist GW3965 (3-[3-[[[2-Chloro-3-trifluoromethyl)-phenyl]methyl](2,2-diphenyl-ethyl)amino]-propoxy]benzene-acetic acid), or none, to serve as experimental group, positive control, or vehicle, respectively. The ALP activities of all groups were analysis after incubation for 48 hours at 37° C. with 5% $CO_2$. Same method for ALP analysis applied as describe in Example 2.

Figure 2:
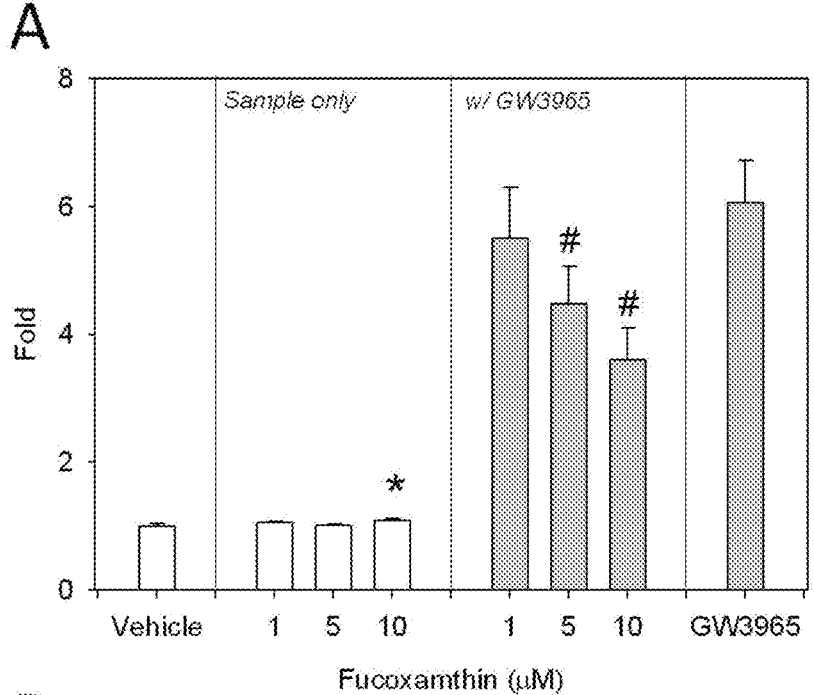
FIG. 2, the transactivation activities of fucoxanthin and fucoxanthinol for LXRβ, wherein (A) represents the transactivation activity of fucoxanthin for LXRβ; (B) represents the transactivation activity of fucoxanthinol for LXRβ; * represents p<0.05, which indicates significant difference when comparing with vehicle; # represents p<0.05, which indicates significant difference when comparing with the positive control.
Figure 2:
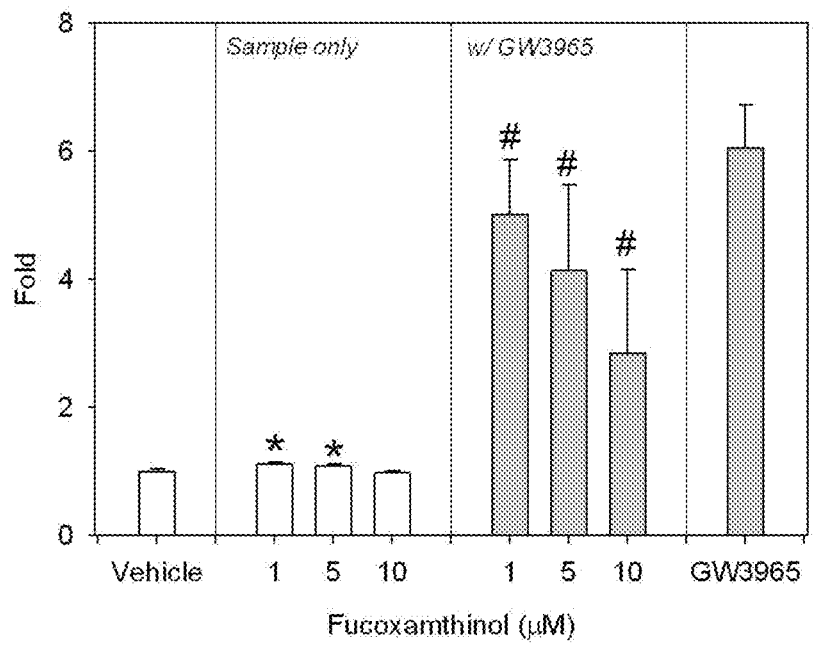

The analytical results of transactivation activities of fucoxanthin and fucoxanthinol for LXRβ are shown in FIG. 2. As shown in FIG. 2(A), 10 μM of fucoxanthin exhibits significant LXRβ transactivation activities ($p<0.05$) which is approximately 2% of the positive control, LXR agonist GW3965; when co-treated with LXR agonist GW3965, the positive control, 5 and 10 μM of fucoxanthin significantly reduced the LXRβ transactivation activity to 69% and 51% of GW3965, respectively ($p<0.05$). On the other hand, as shown in FIG. 2(B), 1 and 5 μM of fucoxanthinol exhibit significant LXRβ transactivation activity ($p<0.05$) which are approximately 3% and 2% of the positive control, LXR agonist GW3965, respectively; when co-treated with LXR agonist GW3965, the positive control, 1, 5 and 10 μM of fucoxanthinol significantly reduced the LXRβ transactivation activity 79%, 62% and 36% of GW3965, respectively ($p<0.05$).

According to this embodiment, for LXRβ, both fucoxanthin and fucoxanthinol shows significant effect on enhancing the transactivation activity of LXRβ; meanwhile, both fucoxanthin and fucoxanthinol show significant antagonistic effects against LXR agonist GW3965. Among which, fucoxanthinol in particular shows more preferable antagonistic effect.

In summary, as shown in Table 3 below, fucoxanthin and fucoxanthinol enhance the transactivation activity of LXRβ less significantly but show antagonistic effects against LXR agonist for both LXRα and LXRβ transactivation activities. The antagonistic effects of fucoxanthin and fucoxanthinol on transactivation activities of LXRα are both more significant than those of LXRβ.

TABLE 3

| | Fucoxanthin | | Fucoxanthinol | |
|---|---|---|---|---|
| | Enhancing effect | Antagonistic effect | Enhancing effect | Antagonistic effect |
| LXRα | — | ↓59% (10 μM) | — | ↓80% (10 μM) |
| LXRβ | ↑2% (10 μM) | ↓49% (10 μM) | ↑3% (1 μM) | ↓64% (10 μM) |

"↑↓" represents significant enhancing or antagonistic percentage; "—" indicates no significant effect.
Enhancing/antagonistic percentage = [($A_{fucoxanthin/fucoxanthinol}$ − $A_{vehicle}$) / ($A_{positive\ control}$ − $A_{vehicle}$)] × 100%

In conclusion, the composition of fucoxanthin and its metabolite, fucoxanthinol, of the present invention are ideal for the regulation of LXR because they are able to selectively activate LXRβ, indicating that both fucoxanthin and fucoxanthinol have partially regulatory effects on LXR without any side effects seen when using conventional artificial agonists. Moreover, fucoxanthin and fucoxanthinol show antagonistic effects when co-administered with LXR agonists, indicating that addition of fucoxanthin and/or fucoxanthinol can reduce the side effects of solely using LXR agonists such as fatty liver caused by accumulation of triglyceride in liver and hypertriglyceridemia.

Hence, fucoxanthin and fucoxanthin of the present invention can be used for regulating LXR in cell and can be used as alternatives or supplements for LXR agonist or antagonist. For example, the composition of the present invention can be utilizing an effective amount of fucoxanthin and its metabolite of the present invention to treat and improve symptoms associated with LXR activity, the composition can further comprise a pharmaceutically acceptable vector. In addition, the fucoxanthin and its metabolites of the present invention can also be used as food composition for improving symptoms associated with LXR activity; such food composition can further comprise an additive, which can be a healthy food ingredient, a food ingredient or a combination thereof. The above healthy food ingredient includes but not limit to citric acid, taurine, vitamin, pantothenic acid, nicotinic acid, or any other substances that are good for the human body; the above food ingredient includes but not limit to vegetable or meat.

The composition for the regulation of liver X receptor in a cell and application thereof provided in present invention is applicable and valuable to the industry. Those embodiments above are better results, and should not, however, be considered to limit the scope of the invention, it is contemplated that modifications will readily occur to those skilled in the art, which modifications will be within the spirit of the invention and scope of the appended claims.

What is claimed is:
1. A method of regulating a liver X receptor (LXR), comprising administering to a subject an effective amount of fucoxanthin or fucoxanthinol, and the fucoxanthin or the fucoxanthinol regulates the transactivation activity of the liver X receptor;
wherein the fucoxanthin is a compound of Formula I:

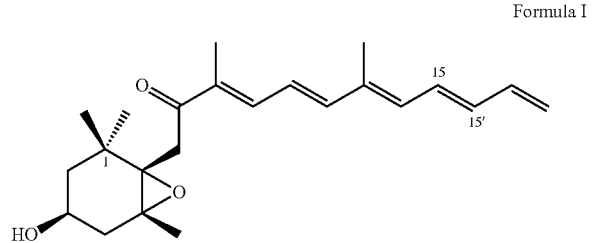

Formula I

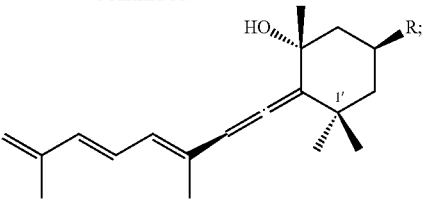

Fucoxanthin, R = OCOCH₃ and
wherein the fucoxanthinol is a compound of Formula II:

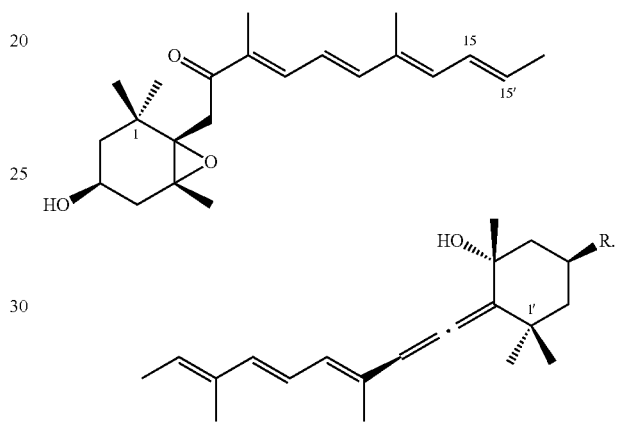

Formula II

Fucoxanthinol, R = OH

2. The method of claim 1, wherein the liver X receptor is LXRα or LXRβ.
3. The method of claim 2, wherein the fucoxanthin or the fucoxanthinol enhances the transactivation activity of LXRβ.
4. The method of claim 2, wherein when the fucoxanthin or the fucoxanthinol is co-administered with a LXR agonist to the subject, the fucoxanthin or the fucoxanthinol antagonizes the transactivation activity of LXRα or LXRβ induced by the LXR agonist.
5. The method of claim 4, wherein the LXR agonist is N-(2,2,2-trifluoroethyl)-N-[4-[2,2,2-trifluoro-1-hydroxy-1-(trifluoromethyl)ethyl]phenyl]-benzenesulfonamide or 3-[3-[[[2-Chloro-3-(trifluoromethyl)-phenyl]methyl](2,2-diphenyl-ethyl)amino]propoxy]benzenacetic acid.

* * * * *